United States Patent [19]
Goldstein et al.

[11] Patent Number: 5,335,673
[45] Date of Patent: Aug. 9, 1994

[54] ORAL COLLECTION DEVICE AND METHOD FOR IMMUNOASSAY

[75] Inventors: Andrew S. Goldstein, Portland; Stefan Gavojdea; David F. Zogg, both of Tigard, all of Oreg.

[73] Assignee: Epitope, Inc., Beaverton, Oreg.

[21] Appl. No.: 26,217

[22] Filed: Mar. 1, 1993

Related U.S. Application Data

[63] Continuation of Ser. No. 865,054, Apr. 8, 1992, abandoned, which is a continuation of Ser. No. 641,739, Jan. 15, 1991, Pat. No. 5,103,836, which is a continuation-in-part of Ser. No. 486,415, Feb. 28, 1990, abandoned, which is a continuation-in-part of Ser. No. 410,401, Sep. 21, 1989, Pat. No. 5,022,409.

[51] Int. Cl.⁵ .............................................. A61B 5/00
[52] U.S. Cl. .................................................. 128/760
[58] Field of Search ............... 128/759, 760, 762, 769, 128/771; 604/1, 312, 358; 206/259

[56] References Cited

U.S. PATENT DOCUMENTS

| | | | |
|---|---|---|---|
| 3,750,645 | 8/1973 | Bennett et al. | 128/760 |
| 4,063,558 | 12/1977 | Smith | 604/358 |
| 4,580,577 | 4/1986 | O'Brien et al. | 604/224 |
| 4,635,488 | 1/1987 | Kremer | 128/760 |
| 4,774,962 | 10/1988 | Hebel et al. | 604/317 |

*Primary Examiner*—Max Hindenburg
*Attorney, Agent, or Firm*—Wegner, Cantor, Mueller & Player

[57] ABSTRACT

A method and device for collecting immunoglobulins and other analytes from the oral cavity for immunological and other testing. The device is a treated absorbent pad used to collect a specimen having a high concentration of immunoglobulins or other analytes. The specimen can be subjected to a basic immunological testing technique which can be used as a tool for screening a patient for diseases. A test kit is also provided.

28 Claims, 4 Drawing Sheets

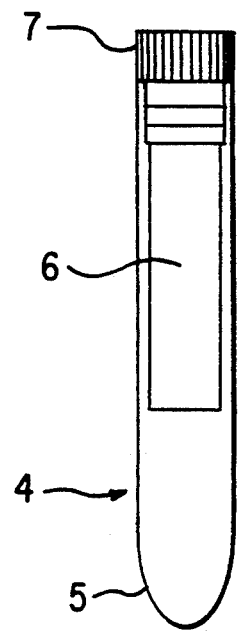
FIG. 3
FIG. 4
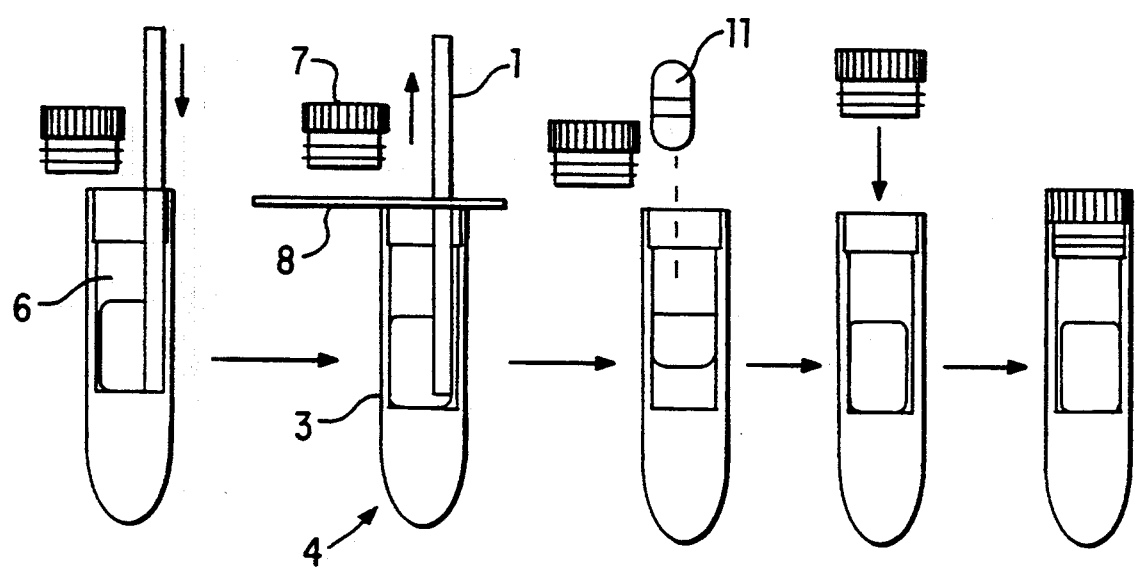

ORAL COLLECTION DEVICE AND METHOD FOR IMMUNOASSAY

CROSS-REFERENCE TO RELATED APPLICATIONS

This application is a continuation of the U.S. application Ser. No. 07/865,054 filed Apr. 8, 1992, now abandoned which is a continuation of Ser. No. 07/641,739 filed Jan. 15, 1991, now U.S. Pat. No. 5,103,836, which is a continuation-in-part of Ser. No. 07/486,415 filed Feb. 28, 1990, now abandoned, which is a continuation-in-part of Ser. No. 410,401 filed Sept. 21, 1989, now U.S. Pat. No. 5,022,409.

BACKGROUND OF THE INVENTION

The present invention relates to the field of immunological testing. In particular, a system for analyzing immunoglobulins and other substances extracted from the oral cavity is disclosed.

The immune system of the mouth not only interacts with the general immune system of the body, but also has its own centralized center for antigen-antibody response. Within the oral cavity is found lymph nodes and intraoral lymphoid aggregations. The extraoral lymph nodes are involved in the drainage of the oral mucosa, gum and teeth. However, the function of the intraoral lymphoid tissue is little understood.

The extraoral lymph nodes include a fine network of lymph capillaries which are superficially located in the mouth, palate, cheeks, lips, gingiva, and pulp of the teeth. The capillaries join to larger lymph vessels which originate from a network deep in the muscle of the tongue and other structures. An antigen can gain entry into the oral lymphatic system directly through the capillaries or be transported there by phagocytes. Once inside the network, the antigen can induce an immune response.

Included in the intraoral lymphoid tissue are generally four distinct tissue aggregations: (a) the tonsils, (b) scattered submucosal lymphold aggregations, (c) salivary gland lymphoid tissue, and (d) gingival lymphoid tissue.

The tonsils (palatine and lingual) primarily produce B-cells and T-cells which are generally contained within a cap of lymphocytes and plasma cells. Antigen typically gains entry into the tonsils through a distinct epithelial region wherein the antigen can come into contact with the T- and B-cells to stimulate an immune response. The predominant type of antibody formed in the tonsils is found to be IgG followed, in order, by IgA, IgM, IgD and IgE.

Scattered submucosal lymphoid cells have not been extensively studied. These cell masses are histologically similar to tonsillar tissue.

Both the major salivary glands (parotid, submandibular and sublingual) and the minor salivary glands have been found to contain lymphocytes and plasma cells. Most of the plasma cells secrete IgA and some IgG or IgM. The IgA synthesized in the salivary glands has a dimeric structure. This type of IgA is referred to as secretory IgA (sIgA) and is the major immunoglobulin component in saliva.

Both T-cells and B-cells are found in the gingival lymphoid tissue. In subjects having clinically normal gingival tissue, T-cells predominate. During an infectionary period, such as during the development of gingivitis, B-cells have been found to predominate.

Plasma cells are also found in the gingival lymphoid tissue. Clusters of these cells are generally located near the blood vessels and predominantly produce IgG. To a lesser extent, IgA and IgM are also manufactured. More importantly, Brandtzaeg et al. in, *Human Saliva: Clinical chemistry and Microbiology* edited by Jorma O. Tenovuo, have shown that the immunoglobulins from the secretions from the gingival tissue area are directly related to the immunoglobulins found in the blood.

Because of the association between immunoglobulins of the blood and saliva, as well as the occurrence of sIgA peculiar to salival fluid, antigen-antibody tests have been conducted on the saliva to assess the value of such tests as a screening tool for diseases.

Collection of saliva from the salivary glands is complicated by the low volumes secreted, the diverse anatomic dispersion of the glands, and the relatively high viscosity of the fluid. Most techniques for collection involve the use of capillary tubes, suction into micropipettes, chewing on paraffin or aspiration into polypropylene syringes. These methods, however, are limited in that viscosity of the saliva makes the recovery of bubble-free material by these techniques difficult. Other methods of collection have been suggested to eliminate or at least reduce the quantity of bubbles in the sample. Among such methods include collecting saliva in the mouth by direct absorption with a sponge or flexible wad of osmotic membrane. After absorption, the saliva can be separated from the absorptive material by centrifugation or by compressing the absorptive material. However, absorption is generally accomplished by using cotton, nylon, or polyester as the absorptive material. These materials can non-specifically bind proteins which can result in an undesirably low recovery of immunoglobulins, Testing of salivary specimens has not been extensively developed. In addition to problems with collection, the samples collected by the known methods typically contain about 0.01–0.1% of the immunoglobulin found in blood serum. Because of the reduced immunoglobulin content of saliva, it has been necessary to use more accurate antigen-antibody assay methods in screening patients for disease. Parry et al., "Rational Programme for Screening Travellers for Antibodies to Hepatitis A Virus", *The Lancet*, Jun. 25, 1988, have discussed such methods and have found that the more accurate IgG-capture radioimmunoassay (GACRIA) test is preferable to avoid false indications which may occur in less accurate methods. Of course, more accurate testing procedures usually require added time and expense to achieve the test results.

BRIEF DESCRIPTION OF THE DRAWINGS

FIG. 3 is a side view of one embodiment of a container for storing the pad;

FIG. 4 is a flow diagram demonstrating how the pad is to be placed and stored in the container of FIG. 3;

SUMMARY OF THE INVENTION

Figure 1A:
FIG. 1a is a side view of the pad and pad holder of the instant invention.

In order to eliminate or greatly reduce the problems inherent in antigen-antibody analysis of salival fluid, the present invention provides a method for collecting immunoglobulins from the oral cavity in a manner highly desirable for use in immunoassays. This method can be accomplished with the aid of a hypertonic solution- The method concerns placing an oral immunoglobulin collecting pad, which has been treated with a hypertonic solution, in the oral cavity to absorb a sufficient quantity of oral immunoglobulin for immunological testing. The use of the pad results in a yield of immunoglobulins greater than would be expected and can incorporate basic antigen-antibody testing techniques as a screening tool for diseases.

The hypertonic solution used in the present invention can also include additives to further provide for an optimal yield in salivary immunoglobulin content. Such additives can include compounds which maintain the correct pH, compounds which preserve the oral immunoglobulins, or compounds which inhibit the growth of organisms. The combination of such compounds provides for the collection of a salival fluid specimen which requires minimum manipulation in preparing the specimen for testing.

We have also found that the present invention can be used to collect substances other than immunoglobulins for testing. In fact, the invention has been successfully used to collect substances having molecular weights ranging from about 176 (cotinine) to about 950,000 (IgM). There is no limit to the size of the molecule which can be collected using the present invention. If the molecule can pass through the walls of the capillaries and other oral tissue, it can be collected using the present invention.

DETAILED DESCRIPTION OF THE INVENTION

The present invention is concerned with collecting oral immunoglobulins for immunological testing and other substances for testing. A treated pad is used to collect a specimen having a high concentration of immunoglobulins or the other substances. High levels of immunoglobulins from the oral cavity are considered to be concentrations in excess of 50 μg total Ig per ml. The specimen can be subjected to a basic testing technique which can be used as a tool for screening a patient for diseases or for the presence of certain foreign substances.

Representative molecules which have been successfully collected by the use of the present invention are:

| Analyte | Molecular Weight |
|---|---|
| Cotinine | 176 |
| Glucose | 180 |
| Theophylline | 180 |
| Cocaine | 303 |
| Beta2-microglobulin | 11,818 |
| Hepatitis B surface antigens | 24,000 |
| Beta-human chorionic gonadotropin | 37,900 |
| IgG -- human antibody | 150,000 |
| Total IgG (antigen not specified) | |
| HIV-1 | |
| Hepatitis A | |
| Hepatitis B | |
| Rubeola (measles) | |
| Syphilis non-treponemal antigen | |
| IgA -- human antibody | 160,000 |
| Total IgA (antigen not specified) | |
| IgM -- human antibody | 950,000 |
| Total IgM (antigen not specified) | |
| Hepatitis A | |
| Hepatitis B | |

The solution to be used in the pad of the present invention is preferably a hypertonic solution. Although a non-hypertonic solution such as water may be used, it has been found that immunoglobulin production from salivation rapidly declines in concentration using such a solution. However, the use of a hypertonic solution results in a constant production of immunoglobulin from other sources within the oral cavity, those sources not being completely understood. By using a hypertonic solution, it is possible to gain an increase of as much as 8–16 times more immunoglobulin than by using distilled water.

A hypertonic solution is a salt solution which has an ionic strength exceeding that found in blood. In general, salts used in the preparation of the hypertonic solution of the present invention are present in an amount of from about 1.5% to about 5% by weight, preferably 3.5% by weight.

Salts which can be used in the preparation of the hypertonic solution include alkali metal compounds as well as alkaline earth metal compounds. Preferred salts include sodium chloride, potassium chloride, magnesium sulfate, magnesium chloride and calcium chloride. Sodium chloride is found to be the least toxic, least expensive and most palatable.

The hypertonic solution of the present invention can also include a compound or ingredient for stimulating salivation. The compounds capable of stimulating salivation are found to exhibit a sour taste. These compounds include weak organic acids. Preferred among the weak organic acids are citric acid, ascorbic acid and acetic acid. It is preferred to use citric acid and ascorbic acid at a concentration of between about 0.05% and 0.5% by weight. The preferable range for acetic acid is between about 0.5% and 3.0% by weight.

In order to minimize degradation in a collected specimen, the hypertonic solution of the present invention can include a preservative. Such a preservative can act to inhibit proteolytic enzymatic activity which can be responsible for the destruction of antibody molecules. Compounds contemplated as a preservative include anti-bacterial agents, anti-fungal agents, bacteriostatic agents, fungistatic agents, and enzyme inhibitors. In a preferred embodiment benzoic acid, sorbic acid or the salts thereof are used as anti-fungal agents. As bacteriostatic agents, salts in high concentration and compounds capable of maintaining the hypertonic solution at low pH are contemplated. Such salts include thimerosal (or merthiolate), phenyl mercuric acetate, phenyl mercuric nitrate and sodium azide. Other preferred preservatives include preservatives which are typically used in medicines and mouthwashes. Examples include ethyl alcohol and chlorhexidine gluconate. Another class of preferred anti-microbial agents are detergents which can be used as topical germicides or in mouthwashes. An example is benzalkonium chloride. It is preferred to use these preservatives in a range of about 0.01% to about 0.2% by weight.

In the present invention, a pad containing the salts of the hypertonic solution is used to absorb saliva and mucosal secretions from the oral cavity. The pad is made of an absorbent material which can be effectively placed into the oral cavity. A plastic or carbohydrate material such as cellulose can be used as the absorbent material, but a thick, absorbent cotton paper is preferred. An example of a thick, absorbent cotton paper is product #300 manufactured by Schleicher and Schuell in Keene, N.H. The pad is preferably not in the form of a foam or sponge, although foam or sponge could be used.

The pad is impregnated with the hypertonic solution by any known means. The hypertonic solution of the present invention could be applied to the pad by dipping the pad into the hypertonic solution so that the salts of the solution can be absorbed into and onto the pad, removing the pad from the solution and allowing the pad to dry. Typically, the pad is dipped into the hypertonic solution and about 1 ml of solution is absorbed. Alternatively, the hypertonic solution could be sprayed onto the pad until a sufficient amount, preferably about 1 ml is absorbed. Excess liquid is shaken off and the pad is placed into a forced air, convection drying oven at 50° C. for 2 hours. After drying, there will be formed a specially treated pad which comprises the salts of the hypertonic solution of the present invention. It is preferred that, as preservatives, such salts as benzalkonium chloride, acetyl pyridinium chloride or chlorhexidine gluconate be used in the preparation of the pad.

Most materials from which the pad is made can nonspecifically bind protein. Thus, some immunoglobulins can undesirably bind to the pad and it is desired to block proteins from binding to the pad by using a blocking agent. Non-specific binding is not normally a problem in the collection of blood samples since blood contains its own blocking agent (i.e., human serum albumin).

To reduce non-specific binding in the collection of oral specimens, a blocking agent can be added to the hypertonic solution to be incorporated into the pad. A blocking agent is generally a soluble protein which is used to prevent non-specific binding of another protein to a solid surface. Compounds which can be added as blocking agents include albumin and gelatin, but any water soluble, non-toxic protein can be used as a blocking agent as long as the protein does not adversely affect antibody molecules. It is preferred to use bovine gelatin. In general, blocking agents can be added to the hypertonic solution of the present invention at a concentration of between about 0.01% and 0.2% by weight. The contents of the hypertonic solution are then incorporated into the pad as described above.

The preferred solution to be used in the preparation of the pad has the following composition:

| component | conc. (wt. %) |
| --- | --- |
| sodium chloride | 3.0% |
| sodium benzoate | 0.1% |

| -continued | |
| --- | --- |
| component | conc. (wt. %) |
| potassium sorbate | 0.1% |
| bovine gelatin | 0.1% |
| distilled water | |
| addition of 0.1N sodium hydroxide to increase pH to about 6.5 | |

Figure 1B:
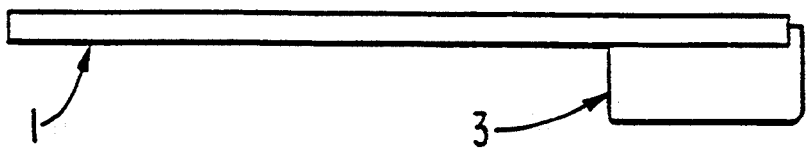
FIG. 1b is top plan view of the pad and pad holder of FIG. 1.

To collect a substance from the oral cavity, the pad can be placed into the mouth with the aid of a holder. The pad and holder are shown in FIGS. 1a and 1b. The pad holder 1 can be a hollow, plastic stick having a groove 2 at one end. The pad 3 is inserted into the groove and the holder can be manipulated to place the pad into the oral cavity, preferably between the lower gums and cheek. Placement of the pad between the lower cheek and gums facilitates absorption of secretions originating from gingival lymphoid tissue as well as secretions from submucosal lymphoid tissue and salivary gland lymphoid tissue. It is preferable that the specimen be collected by rubbing the pad back and forth between the gums and cheek for about ten seconds and then holding the pad in position for about two minutes.

After the specimen has been collected, the pad is stored in a container until immunological testing can be performed. One type of container is shown in FIG. 3. It is desired that the container 4 have a centrifuge tube 5 as an outer portion of the container, and that an inner portion of the container have an inner tube 6 which mounts into the centrifuge tube. The pad is to be placed into the inner tube, and the contents therein are secured by a tube cap 7.

Figure 2:
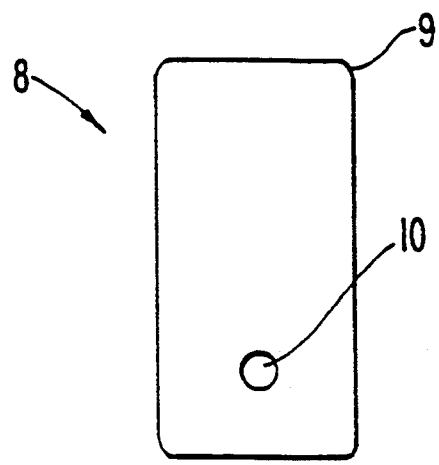
FIG. 2 is a top view if the pad removal device according to one embodiment of the invention.

To place the pad in the inner tube, a pad removal device is used. The device is shown in FIGS. 2 and 4. The pad removal device 8 is preferably a disk 9 which has an opening 10 through which the pad holder 1 can be inserted.

The pad can be inserted into the inner tube and prepared for storage in advance of immunological testing in the manner illustrated in FIG. 4. The tube cap 7 is removed from the container 4, and the pad 3 and holder are inserted into the inner tube 6. The pad removal device 8 is placed over the holder. Then, the pad holder is inserted through the opening of the pad removal device and the holder pulled through the opening to remove the pad. Once the pad is placed in the inner tube, a preservative solution 11 is added. Such a preservative solution can act to inhibit enzymatic activity which can be responsible for the destruction of antibody molecules or can function as an anti-microbial agent.

Compounds contemplated for use in the inner tube as a preservative include anti-bacterial agents, anti-fungal agents, bacteriostatic agents, fungistatic agents, and enzyme inhibitors. As an antibacterial agent, it is preferred to use chlorhexidine gluconate or thimerosal.

The preservative solution to be used in the inner tube can contain one or a combination of the preservatives which can be incorporated into the hypertonic solution of the present invention. In general, the preservatives are included in a concentration which limits microbial contamination and does not adversely effect the immunoglobulins absorbed into the pad.

The preservative solution to be used in the inner tube can also contain a detergent which improves removal of antibody from the pad during centrifugation. Tween 20

(polyoxyethylene sorbitan monooleate) is a preferred detergent since it can also prevent non-specific binding of antibody to a solid surface. It is preferred to use a combination comprising about 0.01%–0.2% chlorhexidine gluconate and 0.2%–0.7% Tween 20. A combination comprising about 0.1% chlorhexidine gluconate and 0.5% Tween 20 is most preferred.

After the preservative solution is added to the inner tube, the tube cap is inserted into the container to seal in the contents. The pad can be stored in this manner for several days until immunological testing can be initiated.

To simplify the collection and analysis of an oral specimen using the pad collection system, a kit can be provided. The kit can include a combination of the treated pad and implements used to collect and prepare the oral specimen for further immunological analysis. One preferred embodiment of the kit includes the treated pad 3 and pad holder 1; the container 4 having the inner tube 6, the outer tube 5 and the cap 7; the pad removal device 8; and the storage preservative 11.

Figure 5:
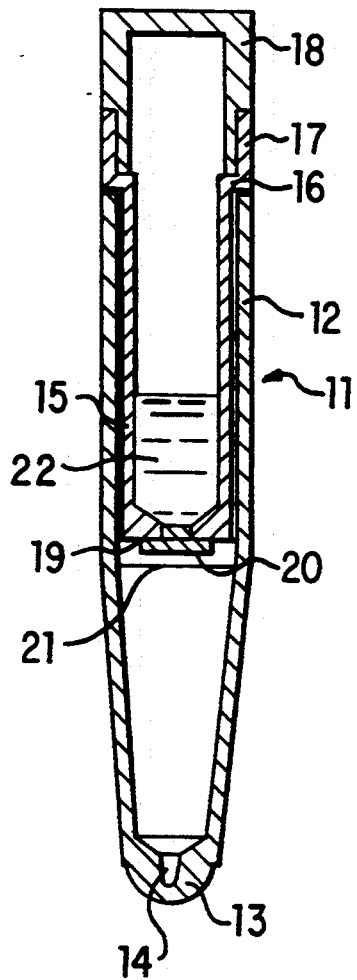
FIG. 5 is a longitudinal section of another embodiment of a container for storing the pad.

Reference is now had to FIG. 5 wherein there is shown a prior art assembly which has been modified for use with the instant invention. The container 11, as disclosed in U.S. Pat. No. 4,774,962, comprises a centrifuge tube 12 having a tapered lower end or base 13 with a downwardly tapering recess 14 in which solid matter accumulates upon centrifugation; an upper tube or container 15 having a radially outwardly projecting annular flange 16 and a cylindrical upper portion 17 at its upper end; and a plug or stopper 18. As taught by U.S. Pat. No. 4,774,962, the cylindrical portion 17 and stopper 18 are of the same size and shape as the upper part of centrifuge tube 12 so they are flush with the outer surface of the centrifuge tube and the assembly presents a uniform appearance, although this feature is not important to the practice of the instant invention. In the floor 19 at the bottom of container 15 is a bore 20 to allow liquid to flow from container 15 to centrifuge tube 12 when the complete assembly is centrifuged. The container 15 is made of any suitable material such as polyethylene, glass, etc. Similarly, the stopper 18 is made of any suitable material such as polyethylene as is well-known in the art.

There are two major differences between the container 11 of FIG. 5 and the assembly of U.S. Pat. No. 4,774,962. First, the prior art assembly contains a cylindrical chewable absorbent elastic body which is chewed by the user until it is sucked full of saliva. The instant invention does not utilize a body to be chewed by the user to absorb saliva although, while it would be awkward due to its size and shape, if it is impregnated with a hypertonic solution and used according to the instant invention it would fall within the scope thereof.

Second, there is a removable plug 21 in bore 20. The plug could be made of any suitable material such as wax, a plastic, etc. A suitable quantity of a preservative solution 22 is placed in the container 15. The preservative solution 22 is the same as that already described by reference to FIGS. 1–4, with the same optional ingredients.

Figure 6:
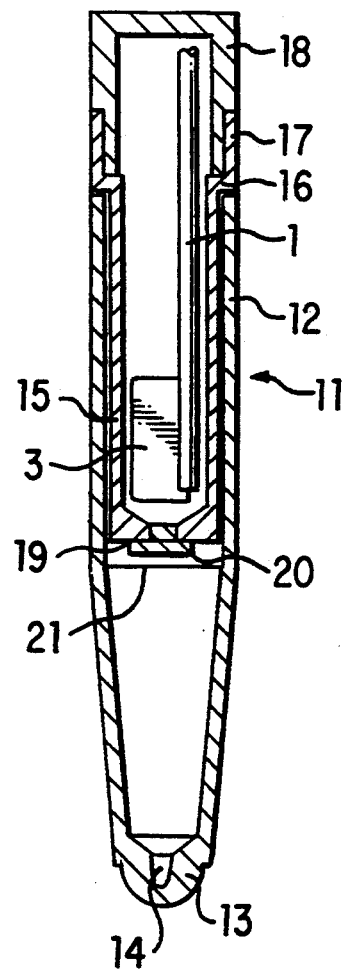
FIG. 6 is a longitudinal section of the embodiment of FIG. 5 with the pad and holder shown.

In this embodiment, the pad 3 on holder 1 is used as already described. After the pad 3 is removed from the user's mouth, stopper 18 is removed from container 15 and the pad is placed within the container 15. The holder 1 is broken off at a point outside the mouth of container 15 so it will project upwardly from the container. Then the stopper 18 is replaced. Since stopper 18 is hollow, it will securely seal the container 15 with the broken end of holder 1 extending into it as shown in FIG. 6. Holder 1 is preferably scored at a suitable location to provide for easy breaking. When the pad 3 is inserted in container 15, it will absorb at least a part of preservative solution 22.

The pad 3 is stored in container 15 until testing can be initiated. At the laboratory, the container 15, with the stopper 18 securely in place, is inverted, the seal 21 of wax or other suitable substance is removed, and the container 15 is placed in a centrifuge tube 12. The complete assembly 11 is then centrifuged whereby all the liquid, including preservative solution, saliva, etc., is dragon down through bore 20 into the centrifuge tube 12. Testing is then performed using known techniques.

As with the first embodiment, to simplify the collection and analysis of an oral specimen using the pad collection system of the second embodiment, a kit can be provided. The kit can include a combination of the treated pad and implements used to collect and prepare the oral specimen for analysis. One preferred embodiment of the kit includes the treated pad 3 and pad holder 1; the container 15 having the stopper 18 and the storage preservative 22. Optionally, a centrifuge tube 12 could be included.

Figure 7:
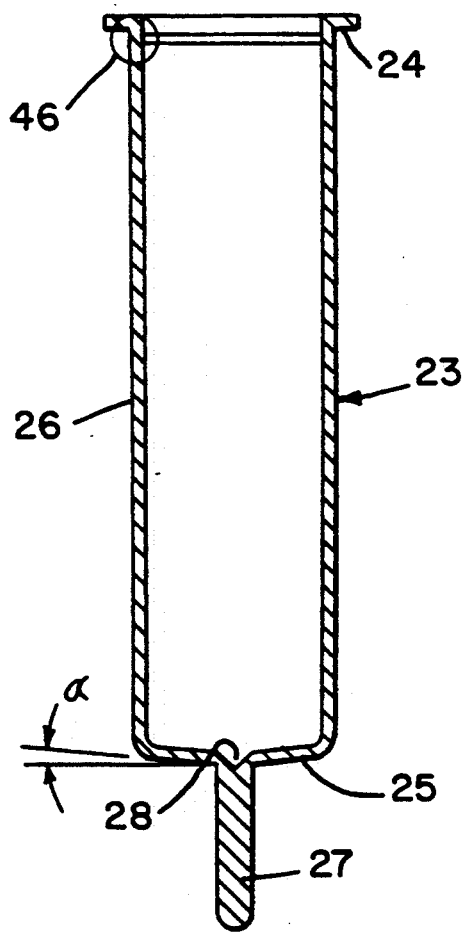
FIG. 7 is a longitudinal section of a container according to a third embodiment.

In still another, preferred, embodiment, a tube having a frangible nipple instead of a wax seal is provided. Reference is made to FIG. 7 which depicts a vial generally designated by the numeral 23 having an open upper end forming an outwardly projecting annular rim or bead 24 and a lower end forming a floor 25. The wall 26 is preferably slightly tapered from the upper end to the floor 25. A nipple 27 extends downwardly from the floor 25. At the center of the inside of the floor 25 is a depression 28, preferably "V" shaped. The depression 25 causes the base end nipple 27 to be weakened, thereby allowing the same to break off when sufficient pressure is applied. The floor 25 preferably has a slight slope at an angle a from the outside to the center. Angle a is preferably about 5°. Container 23 could be made of any suitable material such as polyethylene, glass, etc. The preferred material is a polycarbonate plastic.

Figure 8:
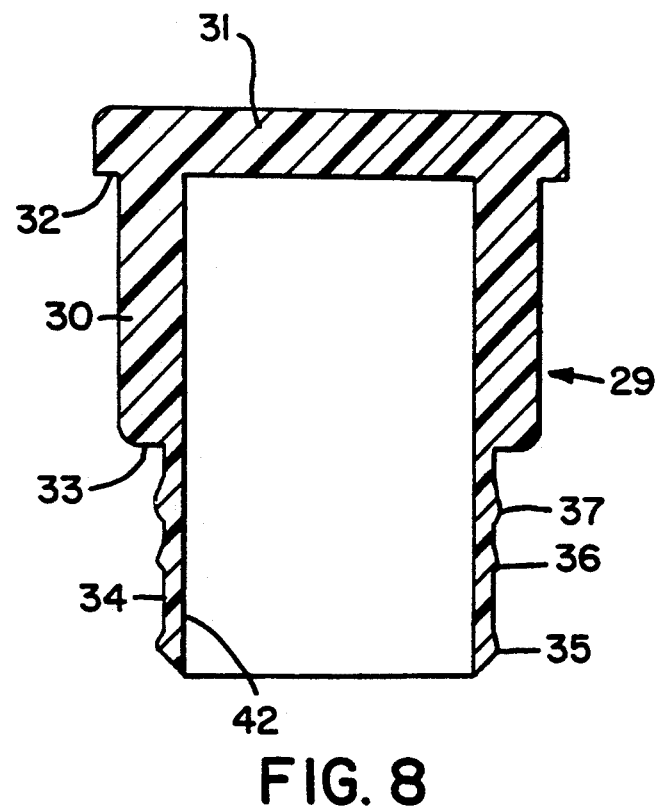
FIG. 8 is a longitudinal section of a stopper for the container of FIG. 7.

Attention is now directed to FIG. 8 wherein there is shown the stopper to be used with container 23. The stopper 29 is hollow and comprises an upper shank portion 30 which is closed at its upper end, the top 31 extending radially outwardly to define an annular flange 32 which is provided for gripping the stopper 29 to remove it from the container 23. The diameter of upper shank portion 30 is approximately the same as that of bead 24 of the container 23. The upper shank portion 30 terminates at its lower end in an annular shoulder 33. Lower shank portion 34 extends downwardly from shoulder 33.

Figure 10:
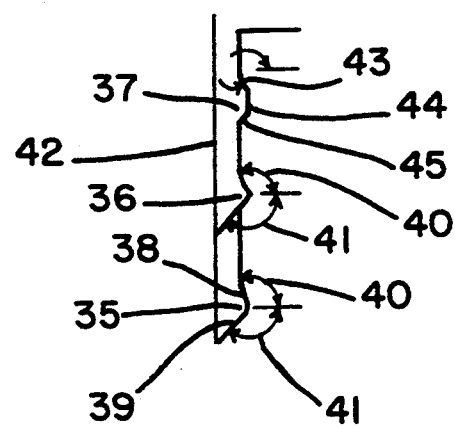
FIG. 10 is an enlarged fragmentary elevational view of a part of the stopper of FIG. 8.

A plurality of annular beads 35, 36, and 37 are formed on the lower shank portion 34. As can be seen in FIG. 10, the lowest bead 35 is pointed with the upper and lower faces 38 and 39, respectively, being at different angles, the preferred angles being shown by arrows 40 and 41. Upper face 33 is preferably at an angle of about 110° from the horizontal while lower face 39 is preferably at an angle of about 45° from the horizontal. As can be seen, lower face 39 tapers downwardly and inwardly from the apex of the bead 35 to the inner wall 42 of stopper 29. Intermediate bead 36 is also pointed with its upper and lower faces at different angles, preferably the same angles as upper and lower faces 38 and 40 of bead 35. Upper bead 37, however, is shaped differently.

Upper bead 37 comprises a linear upper face 43, an essentially vertical linear middle face 44, and a linear lower face 45. Upper face 43 is preferably at an angle of about 70° from the horizontal as depicted by the arrows (not numbered) in FIG. 10. The corners joining upper face 43 and middle face 44, and middle face 44 and lower face 45 are preferably arcuate.

Figure 9:
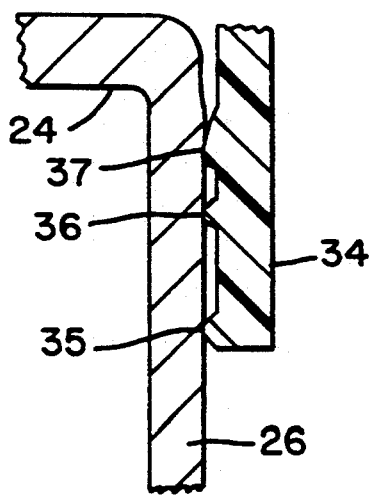
FIG. 9 is an enlarged fragmentary longitudinal section showing a portion of the container of FIG. 7 and the stopper of FIG. 8.

FIG. 9 shows, in enlarged form, the upper portion of container 23 within circle 46 of FIG. 7, with stopper 29 inserted in the mouth of the container 23. The outer diameter of stopper 29 at the outer edges of the beads is slightly larger than the inside diameter of the container 23. The stopper 29 is preferably made of polyethylene, although it can be fabricated of any appropriate resilient material. When the stopper 29 is inserted in the mouth of container 23, beads 35, 36, and 37 are slightly flattened out as shown in FIG. 9 due to the slightly larger diameter of the stopper. This provides a positive seal. In addition, due to the construction of the stopper, inserting and removing the stopper is accomplished in steps, with each bead engaging or disengaging the wall of the container individually, thereby providing control over the use of the stopper.

In use, container 23 is used essentially in the same manner as container 15. The container 23 is supplied with a small amount of preservative solution 22 sealed in by stopper 29. After the pad 3 is used, stopper 29 is removed from container 23, pad 3 is inserted in the container 23, holder 1 is broken off, and stopper 29 is replaced. In the lab, the container 23, with stopper 29 in place, is inverted and frangible nipple 27 is broken off at the weak area caused by depression 28 to leave an opening at the depression 28. A centrifuge tube 12 is placed on container 23 and the necessary test is run.

As with the other embodiments, container 23 could be sold in kit form along with the impregnated pad 3 and holder 1.

The following examples show the effectiveness of the hypertonic solution of the present invention and the pad incorporating the solution of the present invention.

EXAMPLE 1

ELISA Test Data for HIV Antibody—Comparing Serum, Oral Rinse and Oral Pad Eluate The oral rinse solution disclosed in parent application Ser. No. 486,415, filed Feb. 28, 1990, and grandparent application Ser. No. 410,401, filed Sept. 21, 1989, both of which are incorporated by reference herein in their entireties, was prepared except that the pH was adjusted to about 6.0. A pad was prepared using the preferred pad preparation solution of the present invention. Fifteen individuals (12 seropositive, 3 seronegative) are compared for specific antibody levels in serum, rinse derived oral immunoglobulin, and pad derived oral immunoglobulin. A commercial ELISA test was used to detect HIV antibody. This test method shows the relative titer of antibody against the AIDS virus. The results show that in most cases, the pad yields higher antibody concentrations than the rinse.

| PATIENT | SPECIMEN | SEROSTATUS | ELISA RESULTS (O.D. VALUE) (HIGHER NUMBER = STRONGER) |
|---|---|---|---|
| 236 | blood* | (+) | >2.0 |
| | rinse** | | >2.0 |
| | pad*** | | >2.0 |
| 237 | blood | (+) | >2.0 |
| | rinse | | 1.735 |
| | pad | | >2.0 |
| 238 | blood | (−) | 0.077 |
| | rinse | | 0.050 |
| | pad | | 0.051 |
| 239 | blood | (+) | >2.0 |
| | rinse | | 1.423 |
| | pad | | >2.0 |
| 240 | blood | (−) | 0.088 |
| | rinse | | 0.051 |
| | pad | | 0.060 |
| 241 | blood | (−) | 0.751 |
| | rinse | | 0.061 |
| | pad | | 0.052 |
| 242 | blood | (+) | >2.0 |
| | rinse | | 1.537 |
| | pad | | >2.0 |
| 243 | blood | (−) | 0.062 |
| | rinse | | 0.045 |
| | pad | | 0.046 |
| 244 | blood | (+) | >2.0 |
| | rinse | | >2.0 |
| | pad | | 1.981 |
| 245 | blood | (+) | >2.0 |
| | rinse | | 1.742 |
| | pad | | >2.0 |
| 246 | blood | (+) | >2.0 |
| | rinse | | 1.431 |
| | pad | | >2.0 |
| 247 | blood | (+) | >2.0 |
| | rinse | | 1.368 |
| | pad | | >2.0 |
| 248 | blood | (+) | >2.0 |
| | rinse | | 1.492 |
| | pad | | 1.825 |
| 249 | blood | (+) | >2.0 |
| | rinse | | 0.294 |
| | pad | | 0.740 |
| 250 | blood | (+) | >2.0 |
| | rinse | | >2.0 |
| | pad | | >2.0 |
| 251 | blood | (+) | >2.0 |
| | rinse | | >2.0 |
| | pad | | >2.0 |

*Positive blood test results are numbers greater than 0.226.
**Positive rinse test results are numbers greater than 0.241.
*** Positive pad test results are numbers greater than 0.351.

This specimen shows a false positive reaction in the serum and a true negative reaction in the rinse and pad. A negative Western Blot plus additional ELISA testing confirms the false positive reaction in the serum.

EXAMPLE 2

Oral Immunoglobulin Stability Comparison Pad Stored at 37° C. With and Without Preservative A pad was prepared using the preferred pad preparation solution of the present invention. An HIV positive individual was tested to compare immunoglobulin stability of the pad when stored in a distilled water solution and when stored in a preservative solution. The individual was tested by placing two pads in the mouth, one on each side, between the lower cheek and gum. One pad was treated with a gelatin blocking agent. The other pad was treated with the preferred pad preparation solution of the present invention. After removing the pads from the mouth of the individual, the material collected in the gelatin treated pad was eluted with a 0.5 ml solution of 0.3% Tween 20. The material collected in the pad treated with the preferred pad preparation solution was eluted with a 0.5 ml solution of 0.2% chlorhexidine gluconate and 0.3% Tween 20. The extract from each pad was divided into five aliquots. One of the aliquots from each pad was frozen immediately and labelled as time "0" specimen. The other aliquots are stored at 37° C. and tested by ELISA at periods of 1, 3, 7 and 14 days. The time "0" specimen was then thawed and tested by ELISA. The results, as indicated below, show improved preservation of oral immunoglobulin when the preservative solution is used.

| Number of days stored at 37° C. | Preserved specimen ELISA O.D. | Unpreserved specimen ELISA O.D. |
| --- | --- | --- |
| 0 | 1.91 | 1.70 |
| 1 | 1.87 | 1.61 |
| 3 | 1.71 | 1.17 |
| 7 | 1.70 | 1.02 |
| 14 | 1.52 | 0.67 |

EXAMPLE 3

Correlation of Glucose Levels in Blood, Saliva, and sample from Pad

A pad was prepared using the preferred pad preparation solution of the present invention. Ten individuals are tested to compare glucose levels in blood, saliva, and the hypertonic solution-impregnated pad according to the preferred embodiment of the present invention. The material collected in the pad treated with the preferred pad preparation solution was eluted with a 0.5 ml solution of 0.2% chlorhexidine gluconate and 0.3% Tween 20. All glucose tests were done with a Sigma Glucose (HK 20) Quantitative, Enzymatic (Hexokinase) kit according to the manufacturer's directions. The results, as indicated below, show a significant recovery of glucose using the pad of the invention, in all cases greater than the recovery from saliva alone.

| Subject No. | Plasma Glucose μg/dl | Spit Sample Glucose μg/dl | Pad Sample Glucose μg/dl | Ratio Plasma/Pad |
| --- | --- | --- | --- | --- |
| 1. | 107.8 | 7.8 | 31.0 | 3.5 |
| 2. | 84.5 | 4.3 | 13.8 | 6.1 |
| 3. | 124.6 | 15.1 | 21.2 | 5.9 |
| 4. | 89.2 | 15.1 | 16.4 | 5.4 |
| 5. | 98.8 | 6.0 | 11.2 | 8.8 |
| 6. | 94.0 | 23.3 | 32.3 | 2.9 |
| 7. | 122.0 | 6.0 | 17.7 | 6.9 |
| 8. | 84.5 | 16.0 | 18.5 | 4.6 |
| 9. | 138.8 | 9.5 | 15.5 | 9.0 |
| 10. | 121.1 | 363.0 | 450.4 | — |

EXAMPLE 4

A pad was prepared using the preferred pad preparation solution of the present invention. Twenty individuals are tested to compare theophylline levels in serum and the hypertonic solution-impregnated pad according to the preferred embodiment of the present invention. The material collected in the pad treated with the preferred pad preparation solution was eluted with a 0.5 ml solution of 0.2% chlorhexidine gluconate and 0.3% Tween 20. Theophylline levels were determined on an Instrument Laboratories (IL Test™) theophylline test instrument (Cat. No. 35228) according to manufacturer's directions.

| Theophylline Correlation -- Serum Versus Eluate from Pad | | |
| --- | --- | --- |
| Patient No. | Serum Theophylline (UG/ML) | Pad Eluate Theophyllin (UG/ML) |
| 1 | 6.7 | 3.2 |
| 2 | 8.5 | 3.5 |
| 3 | 8.8 | 2.6 |
| 4 | 9.2 | 3.1 |
| 5 | 9.7 | 3.6 |
| 6 | 10.0 | 4.5 |
| 7 | 11.3 | 3.4 |
| 8 | 12.3 | 4.3 |
| 9 | 12.3 | 6.3 |
| 10 | 12.7 | 6.0 |
| 11 | 13.5 | 7.2 |
| 12 | 15.1 | 6.5 |
| 13 | 16.6 | 8.6 |
| 14 | 17.6 | 8.3 |
| 15 | 17.7 | 8.6 |
| 16 | 19.5 | 10.1 |
| 17 | 20.4 | 8.1 |
| 18 | 24.5 | 11.4 |
| 19 | 27.7 | 13.3 |
| 20 | 27.9 | 17.8 |

The results, as indicated above, show a significant recovery of theophylline using the pad of the invention.

EXAMPLE 5

A number of the analytes collected from the mouth by the pad of this invention were measured by means of a "dot blot" system. In this system, two microliter samples of the eluate from the pad (and serial dilutions of this eluate) are dotted on a nitrocellulose strip. After drying and blocking of each strip, the strips are incubated with a dilute solution of a goat or rabbit antibody specific for the analyte to be tested. After washing, the strips are incubated with a peroxidase-conjugated antibody to the goat or rabbit primary antibody. Subsequent incubation with the peroxidase substrate diaminobenzidene (dab) reveals dark brown dots at the place of the original dot of the pad eluate, if that sample contained the analyte of interest. In the case of the tests for total IgG, IgA, and IgM, the pad eluate was dotted on the strips, which was subsequently dried and blocked. This was followed by incubation with a peroxidase-conjugated goat antibody specific for the human antibody class of interest. As above, the dots are revealed by incubation with dab.

Using these systems, the following substances were detected in the pad eluate obtained from normal human subjects:

beta-2-microglobulin
albumin
transferrin
total human IgG (antigen not specified)
ceruloplasmin
total human IgA (antigen not specified)
total human IgM (antigen not specified)

EXAMPLE 6

Hepatitis A (IgM) Saliva Study

A pad was prepared using the preferred pad preparation solution of the present invention. Two groups of individuals are tested to compare hepatitis A levels in saliva and the hypertonic solution-impregnated pad according to the preferred embodiment of the present invention. The material collected in the pad treated with the preferred pad preparation solution was eluted with a 0.5 ml solution of 0.2% chlorhexidine gluconate and 0.3% Tween 20. An ELISA test was used and readings taken of optical density. The results were as follows:

| Subject | Saliva Code | Pad Eluate O.D. | Interpret'n |
|---|---|---|---|
| 1 | | 0.97 | pos. |
| 2 | | 1.02 | pos. |
| 3 | | 0.9 | pos. |
| 4 | | 1.1 | pos. |
| 5 | | 1.02 | pos. |
| 6 | | 1.1 | pos. |
| 7 | | 0.58 | pos. |
| 8 | | 1.02 | pos. |
| 9 | | 1.13 | pos. |
| 10 | | 1.1 | pos. |
| 11 | | 1.32 | pos. | cutoff values for subjects 1–11 were 0.190–0.171 (Abbott Test)

| Subject | Saliva Code | Pad Eluate O.D. | Interpret'n |
|---|---|---|---|
| | 1444 | 0.872 | pos. |
| | 2316 | 0.741 | pos. |
| | 583 | 0.833 | pos. |
| | 392 | 0.81 | pos. |
| | 1297 | 0.752 | pos. |
| | 2723 | 0.626 | pos. |
| | 1179 | 0.606 | pos. |
| | 822 | 0.862 | pos. |
| | 2232 | 0.861 | pos. |
| | 2169 | 0.917 | pos. |
| | 4583 | 0.901 | pos. |
| | 3287 | 0.92 | pos. |
| | 1108 | 0.788 | pos. |
| | 803 | 0.399 | pos. |

-continued

| Subject | Saliva Code | Pad Eluate O.D. | Interpret'n |
|---|---|---|---|
| | 2321 | 0.987 | pos. |
| | 3852 | 1.05 | pos. |
| | 2502 | 0.789 | pos. |
| | 2927 | 1.05 | pos. |
| | 4435 | 0.259 | pos. |
| | 1822 | 0.812 | pos. |
| | 3652 | 0.986 | pos. |
| | 4056 | 0.31 | pos. |
| | 2433 | 0.947 | pos. |
| | 1877 | 0.953 | pos. | cutoff values for subjects in second group were 0.148–0.177 (Abbott Test

EXAMPLE 7

Hepatitis A (Total Antibody)

Saliva Longitudinal Study

A test for total antibody to hepatitis A was run using the same pad and procedure as in the previous Examples. The results are shown in the following table.

| HEPATITIS A (TOTAL ANTIBODY) SALIVA LONGITUDINAL STUDY | | | | | | | | |
|---|---|---|---|---|---|---|---|---|
| Subject | Sample No. | Date | Days From Onset | Cutoff | Blood O.D. | Interpret | Pad O.D. | Interpret |
| 002A | 002A-1 | 3/19/90 | d16 | 0.526 | 0.089 | pos. | 0.255 | pos. |
| | 002A-2 | 4/5/90 | d33 | " | 0.084 | pos. | 0.116 | pos. |
| | 002A-3 | 4/18/90 | d46 | " | 0.084 | pos. | 0.116 | pos. |
| | 002A-4 | 5/2/90 | d60 | " | 0.075 | pos. | 0.095 | pos. |
| | 002A-5 | 5/16/90 | d74 | " | 0.08 | pos. | 0.083 | pos. |
| | 002A-6 | 6/13/90 | d102 | " | 0.05 | pos. | 0.083 | pos. |
| | 002A-7 | 7/11/90 | d130 | " | 0.052 | pos. | 0.082 | pos. |
| 003A | 003A-1 | 4/11/90 | d30 | " | 0.058 | pos. | 0.257 | pos. |
| | 003A-2 | 5/9/90 | d58 | " | 0.053 | pos. | 0.148 | pos. |
| | 003A-3 | 5/23/90 | d72 | " | 0.053 | pos. | 0.117 | pos. |
| | 003A-4 | 6/7/90 | d87 | " | 0.046 | pos. | 0.191 | pos. |
| | 003A-5 | 6/21/90 | d101 | " | 0.054 | pos. | 0.088 | pos. |
| | 003A-6 | 7/17/90 | d127 | " | 0.048 | pos. | 0.108 | pos. |
| | 003A-7 | 8/14/90 | d155 | " | 0.045 | pos. | 0.149 | pos. |
| 005A | 005A-1 | 5/23/90 | d38 | " | 0.046 | pos. | 0.071 | pos. |
| | 005A-2 | 6/7/90 | d53 | " | 0.04 | pos. | 0.042 | pos. |
| | 005A-3 | 6/21/90 | d67 | " | 0.048 | pos. | 0.053 | pos. |
| | 005A-4 | 7/3/90 | d78 | " | 0.049 | pos. | 0.063 | pos. |
| | 005A-5 | 7/17/90 | d83 | " | 0.074 | pos. | 0.031 | pos. |
| | 005A-6 | 8/14/90 | d121 | " | 0.143 | pos. | 0.027 | pos. |
| | 005A-7 | 9/17/90 | d155 | " | 0.144 | pos. | 0.032 | pos. |
| 007A | 007A-1 | 5/31/90 | d23 | " | 0.049 | pos. | 0.236 | pos. |
| | 007A-2 | 6/14/90 | d37 | " | 0.043 | pos. | 0.303 | pos. |
| | 007A-3 | 6/29/90 | d52 | " | 0.043 | pos. | 0.391 | pos. |
| | 007A-4 | 7/12/90 | d65 | " | 0.038 | pos. | 0.134 | pos. |
| | 007A-5 | 8/23/90 | d107 | " | 0.043 | pos. | 0.126 | pos. |
| | 007A-7 | 9/19/90 | d134 | " | 0.039 | pos. | 0.134 | pos. |
| 008A | 008A-1 | 7/17/90 | d24 | " | 0.047 | pos. | 0.081 | pos. |
| | 008A-2 | 7/31/90 | d38 | " | 0.049 | pos. | 0.082 | pos. |
| | 008A-3 | 8/23/90 | d61 | " | 0.042 | pos. | 0.046 | pos. |
| | 008A-4 | 8/31/90 | d89 | " | 0.037 | pos. | 0.044 | pos. |
| | 008A-5 | 9/13/90 | d82 | " | 0.05 | pos. | 0.083 | pos. |
| | 008A-6 | 10/11/90 | d110 | " | 0.041 | pos. | 0.031 | pos. |
| | 008A-7 | 11/12/90 | d142 | " | 0.048 | pos. | 0.028 | pos. |
| 006A | 0906A-1 | 5/29/90 | d46 | " | 0.041 | pos. | 0.148 | pos. |
| 010A | 010A-1 | 6/22/80 | d17 | " | 0.057 | pos. | 0.155 | pos. |

THIS IS AN ABBOTT COMPETITIVE TEST FOR TOTAL ANTIBODY TO HEP A POSITIVE CONTROL = 0.094; NEGATIVE CONTROL = 0.959

EXAMPLE 8

Hepatitis B Surface Antigen (HBsAg)

Hepatitis B surface antigen was detected in saliva samples collected with the pad using the Auszyme™ test kit made by Abbot, Inc. The mean negative control value was −0.003 and the mean positive control was 2.091. The cutoff value was calculated to be 0.047. The results are as follows:

| sample # | Abbott Auszyme HBsAG (pad) |
|---|---|
| 001-B | 0.891 (+) |
| 30-M | 3.352 (+) |
| 38-M | 3.352 (+) |
| 68-M | 1.568 (+) |

EXAMPLE 8

IgM Antibodies to Hepatitis B Core Antigen (HBcAg)

IgM antibodies to Hepatitis B core antigen were detected in saliva samples collected with the Pad using the Corzyme-M$^{TM}$ test kit made by Abbott, Inc. The mean negative control value was 0.058 and the mean positive control was 1.023. The cutoff value was calculated to be 0.314.

| sample # | Abbott Corzyme-M IgM anti-HBc (pad) |
|---|---|
| 30-M | 1.492 (+) |
| 38-M | 2.206 (+) |

EXAMPLE 9

IgG antibodies to Hepatitis B core antigen (HBcAg)

IgG antibodies to Hepatitis B core antigen were detected in saliva samples collected with the pad using the OraQuick assay of the assignee hereof. The OraQuick assay is an ELISA-type assay that utilizes recombinant hepatitis B core antigen and a goat antibody specific for human IgG antibody. Positive controls demonstrated a color with intensity in the range of "+" to "+++". Negative controls were colorless ("−").

| sample # | Epitope OraQuick IgG anti-HBc (pad) |
|---|---|
| 4-M | + |
| 8-M | ++ |
| 32-M | ++ |
| 38-M | ++ |
| 43-M | + |
| 69-M | + |

EXAMPLE 10

Feasibility Study Measles IgG

A feasibility study using the pad of the invention to collect samples for measuring on measles IgG was conducted. A Pharmacia IgG ELISA kit was used for the tests.

| KIT CONTROLS | O.D. 492 |
|---|---|
| High positive | 1.395 |
| Low positive | 0.958 |
| Low positive | 0.948 |
| Neg control | 0.060 |
| Neg control | 0.044 |
| Background | 0.050 |

| PATIENT # | PAD OD | RESULTS |
|---|---|---|
| 216 | 0.729 | + |
| 219 | 0.744 | + |
| 221 | 0.735 | + |
| 222 | 0.673 | + |
| 223 | 0.111 | + |
| 227 | 0.169 | + |
| 230 | 0.176 | + |
| 237 | 0.276 | + |
| 238 | 0.561 | + |
| 248 | 0.535 | + |
| 250 | 0.163 | + |
| 252 | 0.112 | + |
| 254 | 0.178 | + |
| 255 | 0.425 | + |

14 of 14 samples positive 100% correlation
calculated cutoff value = mean of the negatives × 2 = 0.104 (0.052 × 2 = 0.104)

EXAMPLE 11

Detection of Antibody to Syphilis Non-Treponemal Antibodies in Pad Samples

Positive samples were identified among samples from S.F. General Hospital by testing sera on the RPR Card Test from Becton-Dickinson. An ELISA-type membrane assay ("rapid assay" was developed using the cardiolipinphosphatidyl choline-cholesterol mixture spotted on an Immobilon membrane. This was followed by blocking and 1) exposure to serum or saliva samples, 2) washing, 3) exposure to peroxidase conjugated-goat antibody to human IgG, 4) washing, 5) exposure to TMB chromagen. Results were as follows:

| Sample # | RPR Card Test | Serum Result on ELISA | Saliva (OraSure) Result on ELISA |
|---|---|---|---|
| 169 | pos. | pos. | pos. |
| 196 | pos. | pos. | pos. |
| control | neg. | neg. | neg. |

EXAMPLE 12

| β-HCG Levels in Pad Saliva | |
|---|---|
| | HCG Concentration* mIU/ml |
| Negative Controls: | |
| "1" | 0.9 |
| "2" | 0.4 |
| Pregnant Patients: | |
| "A" | 3.9 |
| "B" | 15.2 |
| "C" | 2.1 |

*Determined using the Abbott β-HCG 15/15 Enzyme Immunoassay kit. The Point-to-Point quantitative procedure was followed.

Although many embodiments of the present invention are disclosed, it is to be understood that these embodiments are not limiting. For example, many components can be incorporated into the hypertonic solution of the present invention. The disclosed components represent specific examples which are capable of yielding an increased immunoglobulin concentration in oral specimens. Of course, any list of components cannot be exhaustive and alternatives can be predicted within the scope of the contemplated invention.

What is claimed is:

1. A method of preferentially collecting mucosal transudate from an oral cavity for testing comprising the steps of:
    (a) inserting an absorbent pad into the oral cavity,
    (b) contacting the pad with the oral mucosa without masticating said pad,
    (c) removing the pad from the oral cavity, and (d) preserving the pad for subsequent removal of the collected mucosal transudate from the pad for testing.

2. The method of claim 1, wherein the pad is stored in a container when the pad is removed from the oral cavity.

3. The method of claim 2, wherein the container includes a preservative solution.

4. The method of claim 3, wherein the preservative solution includes chlorhexidine gluconate or thimerosal.

5. The method of claim 4, wherein the preservative solution includes chlorhexidine gluconate.

6. The method of claim 2, wherein the container comprises an open upper end sealed with a removable stopper and a lower end having an opening communicating the interior of the container with the outside, said opening being selectively sealed during storage of said pad and unsealed for said removal of said collected mucosal transudate for subsequent testing.

7. The method of claim 6, wherein said opening is selectively sealed by a removable wax seal.

8. The method of claim 6, wherein said opening is selectively sealed by a removable resilient seal.

9. The method of claim 6, wherein said opening is selectively sealed by a frangible nipple.

10. The method of claim 1, wherein said mucosal transudate containing substances which are analytes having a molecular weight from about 176 to about 950,000.

11. The method of claim 10, wherein said analytes are selected from the group consisting of cotinine, glucose, theophylline, cocaine, beta 2-microglobulin, Hepatitis B surface antigens, beta-human chlorionic gonadotropin, and immunoglobulins, and mixtures thereof.

12. The method of claim 11, wherein said substances are immunoglobulins.

13. The method of claim 12, wherein said immunoglobulins are selected from the group consisting of IgG, IgA, IgE, and IgM.

14. The method of claim 12, wherein said immunoglobulins are antibodies against at least one of a member of the group consisting of HIV, hepatitis A, hepatitis B, rebeola, and symphilis nontreponemal antigen.

15. The method of claim 1 wherein said analysis is by immunological testing.

16. The method of claim 15, wherein said immunological test is an ELISA test.

17. The method of claim 1, wherein the pad is made of a carbohydrate material.

18. A method for recovering mucosal transudate which has been preferentially collected in an absorbent pad for testing, wherein the pad is stored in a container after removal from the oral cavity, wherein said container comprises an open upper end sealed with a removable stopper and a lower end having an opening communicating the interior of the container with the outside, said opening having a removable seal thereon during storage of said pad, said method comprising providing a preservative solution in said container prior to storing said pad within said container, eluting said mucosal transudate with a solvent or diluent therefor within said container, removing said seal, placing said container in a centrifuge tube with the lower end of said container within the centrifuge tube to form an assembly, and centrifuging said assembly to thereby draw said solvent or diluent containing said mucosal transudate into said centrifuge tube.

19. The method of claim 18, wherein the preservative solution includes chlorohexidine gluconate or thimerosal.

20. The method of claim 19, wherein the preservative solution includes chlorohexidine gluconate.

21. The method of claim 18, wherein said seal is a removable wax seal.

22. The method of claim 18, wherein said seal is a removable resilient seal.

23. The method of claim 18, wherein said seal is a frangible nipple.

24. A kit for preferentially collecting and storing mucosa preferentially transudate for subsequent testing comprising a pad and a container for storing the pad; said container containing a preservative solution and comprising an open upper end adapted to be sealed with a removable stopper and a lower end having an opening communicating the interior of the container with the outside, said opening being selectively sealed during storage of said mucosal transudate and unsealed for removal of said collected mucosal transudate for subsequent testing.

25. The kit of claim 24, further comprising a removable stopper.

26. The kit of claim 24, wherein said opening is selectively sealed by a removable wax seal.

27. The kit of claim 24, wherein said opening is selectively sealed by a removable resilient seal.

28. The kit of claim 24, wherein said opening is selectively sealed by a frangible nipple.

* * * * *